United States Patent [19]

Buehler et al.

[11] Patent Number: 4,869,902

[45] Date of Patent: Sep. 26, 1989

[54] ANTACID COMPOSITION

[75] Inventors: John D. Buehler, Germantown, Tn.; Joseph R. Luber, Lafayette Hills; Wayne M. Grim, Doylestown, both of Pa.

[73] Assignee: Rorer Pharmaceutical Corporation, Fort Washington, Pa.

[21] Appl. No.: 191,836

[22] Filed: May 9, 1988

Related U.S. Application Data

[63] Continuation of Ser. No. 916,623, Oct. 8, 1986, abandoned, which is a continuation of Ser. No. 601,796, Apr. 19, 1984, abandoned.

[51] Int. Cl.$^4$ .................... A61K 33/12; A61K 33/10; A61K 33/08
[52] U.S. Cl. .................... 424/686; 424/683; 424/690
[58] Field of Search .................... 514/156, 155, 157

[56] References Cited

U.S. PATENT DOCUMENTS

| | | | |
|---|---|---|---|
| 3,857,938 | 12/1974 | Rovati et al. | 424/156 |
| 4,140,760 | 2/1979 | Withington | 424/81 |
| 4,447,417 | 5/1984 | Spickett et al. | 424/156 |
| 4,482,542 | 5/1984 | Schneider | 424/156 |

OTHER PUBLICATIONS

*Handbook on Nonprescription Drugs,* Fifth ed. pub. by American Pharm. Assoc., Wash., D.C., pp. 9 & 10.

*Primary Examiner*—Frederick E. Waddell

[57] ABSTRACT

A pharmaceutical composition including magnesium alginate and an antacid material useful in the treatment of reflux esophagitis.

13 Claims, No Drawings

ANTACID COMPOSITION

This is a continuation of Ser. No. 06/916,623, filed Oct. 8, 1986, now abandoned, which is a continuation of Ser. No. 06/601,796, filed Apr. 19, 1984, abandoned.

FIELD OF THE INVENTION

The present invention relates to pharmaceutical compositions and particularly to compositions for use in treating gastroesophageal and gastrointestinal irritations.

Esophageal pain, commonly experienced as heartburn, is symptomatic of gastric reflux. Gastric reflux occurs when small amounts of gastric juice and/or bile acids pass into the lower part of the esophagus and cause esophageal irritation. Typically, gastric reflux, which occurs after meals, especially large meals, is aggravated by bending over or lying down, and is a common occurence in patients having a hiatal hernia, or a weakening of the esophageal sphincter. Severe episodes of gastric reflux may inflame the esophageal mucosa and lead to the more serious condition of reflux esophagitis in which severe damage or loss of squamous epithelium of the lower part of the esophagus may occur. If esophagitis is persistent or severe, an inflammatory blockage of the esophagus may develop.

The invention relates to a composition useful in the treatment of reflux esophagitis.

Reported Developments

Persistent gastric reflux has been treated by attempting to reduce gastric volume, acidity of the gastric contents, and accelerate gastric emptying. Reduction in gastric pH is commonly effected by frequent ingestion, for example, in hourly intervals, of antacid preparations such as aluminum hydroxide gel. Other methods include the administration of drugs such as bethanechiol (Urecholine®) and metachlopramide (Reglan®), which increase the tone of the lower esophageal sphincter and accelerate gastric emptying. If these methods do not reverse the inflammatory process, surgical therapy is often recommended.

Another approach to the problem of gastric reflux comprises the administration of a preparation which forms a foam or raft which floats on the stomach contents. The foam containing antacid precedes the stomach contents into the esophagus when reflux occurs and helps to protect the mucosa from further irritation. The gelatinous foam is formed by the combination of an acid insoluble gelatinous material entrapping $CO_2$ gas. Heretofore known preparations used to create the foam comprise sodium bicarbonate and either solid compositions or liquid suspensions of alginic acid or its sodium salt. Exemplary of such prior art preprarations include the product Gaviscon® (Marion Laboratories) and compositions described in U.S. Pat. No. 4,140,760.

Such known compositions contain relatively small amounts of antacid material and relatively large amounts of sodium. Accordingly, they are not particularly effective when used by patients who require a substantial adjustment of gastric pH and/or problems can be encountered when they are used by patients who should not receive an excessive amount of sodium.

SUMMARY OF THE INVENTION

The present invention relates to a low-sodium antacid composition useful in the treatment of reflux esophagitis prepared from magnesium alginate and an effective acid-neutralizing amount of an antacid.

Another aspect of the present invention relates to an antacid composition comprising magnesium alginate and a combined form of magnesium carbonate and aluminum hydroxide, and particularly to aqueous suspensions comprising the aforesaid ingredients.

DETAILED DESCRIPTION

Magnesium alginate, one of the essential materials for use in the present invention, can be prepared from alginic acid, which, like its salts such as sodium alginate, is a polymeric material composed of 1,4' linked residues of $\alpha$-D-mannuronic acid and $\beta$-L-guluronic acid. The proportions of mannuronic to guluronic acid residues varies and depends on the brown algae source from which the alginate is extracted. Table 1 shows the composition of alginic acid obtained from various types of commercially important brown algae.

TABLE 1

Mannuronic Acid (M) and Guluronic Acid (G) Composition of Alginic Acid Obtained from Commercial Brown Algae

| Species | M Content (%) | G Content (%) | M/G Ratio | M/G Ratio Range |
|---|---|---|---|---|
| Macrocystis pyrifera | 61 | 39 | 1.56 | — |
| Ascophyllum nodosum | 65 | 35 | 1.85(1.1) | 1.40–1.95 |
| Laminaria digitata | 59 | 41 | 1.45 | 1.40–1.60 |
| Laminaria hyperborea (stipes) | 31 | 69 | 0.45 | 0.40–1.00 |
| Ecklonia cava and Eisenia bicyclis | 62 | 38 | 1.60 | — |

A thorough discussion of the structure and properties of alginic acid and a number of its commercially available salts is found in the trade publication of Kelco, Division of Merck and Co., Inc., entitled "Algin/hydrophilic derivatives of alginic acid for scientific water control" (second edition).

The varying composition of alginic acid and its derivatives is reflected in variations in certain of its physical properties including viscosity. Viscosity measurements of commercially available alginates using a Brookfield Model LVF Viscometer at 60 rpm with the appropriate spindle at 25° C. of 1 to 2% solutions range from about 10 cps to about 17,000 cps.

The pharmaceutical composition according to the present invention uses the magnesium salt of alginic acid and preferably magnesium alginate exhibiting a viscosity in a 7.5 wt % solution, measured at 25° C. by the Brookfield Model LVT Viscometer at 12 rpm, using spindle no. 2, of about 10 to about 1700 cps, and preferably about 100 to about 1000 cps.

The magnesium alginate may be prepared by a number of methods, but the preferred method comprises the reaction in aqueous media of magnesium carbonate and alginic acid, followed by the adjustment of the pH of the reaction mixture to about 7.5. The preferred alginic acid used to prepare the magnesium salt comprises a polymer chain of mannuronic acid and guluronic acid segments in a ratio of mannuronic to guluronic acid of about 0.4:1 to about 2:1, and most preferably about 0.4:1 to about 1:1. In terms of weight percent, it is preferred that the alginic acid comprise about 28 to about 35 wt % of mannuronic acid and about 65 to about 72 wt % of guluronic acid. One species of brown algae which provides the most preferred source of alginic acid is *Laminaria hyperborea*.

The pharmaceutical composition according to the present invention includes an antacid material. The antacid material is preferably present in an amount at least sufficient to neutralize excess gastric acid present in the stomach. The weight ratio of antacid material to magnesium alginate ranges from about 1:1 to about 2:1. Exemplary antacid materials include magnesium hydroxide, aluminum hydroxide, magnesium carbonate, magnesium trisilicate, magaldrate, and mixtures thereof.

The preferred antacid material comprises magnesium carbonate and aluminum hydroxide as separate ingredients and/or in a combined form. This includes codried powders of magnesium carbonate and aluminum hydroxide, and compounds such as the hydrotalcites having a formula $(Al)_w(Mg)_x(OH)_y(CO_3)_z$ and described in U.S. Pat. No. 4,351,814, hereby incorporated by reference. Preferred combined forms of material include $Al(OH)_3$ in an amount of about 30 to about 40 wt % (as $Al_2O_3$), and $MgCO_3$ in an amount of about 10 to about 20% (as MgO). A preferred composition is sold by Societe Des Products Chemiques Alumineux (SPCA) and contains about 35% $Al_2O_3$ and about 12% MgO.

The pharmaceutical composition of the present invention can be used in tablets, powders or liquids. The liquid compositions are preferably aqueous suspensions in which the amount of antacid material provides an acid neutralizing capacity of about 1 to about 3 mEq/ml of suspension. The tablet compositions include an amount of antacid material in each tablet which provides an acid neutralizing capacity equal to about 5 to about 10 ml of said aqueous suspension.

The pharmaceutical compositions of the present invention are substantially sodium free, that is, sodium is present in no more than about 10 mg per dosage amount or about 10 mg per 10 ml of the aqueous suspension of the present invention.

Certain embodiments of the present invention may include a material which produces a nontoxic gas when contacted with aqueous acid such as gastric acid. The gas-producing material may also function as the antacid material or be a separate ingredient in the composition. The preferred gas-producing material is potassium bicarbonate.

The compositions of the present invention which include a gas-producing material form a gas, after ingestion, as a result of reacting with gastric acid in the stomach. The gas is trapped in the alginic acid gel formed by the composition thereby creating a gelatinous foamy mass of lower bulk density than the gastric contents. The gelatinous mass floats to the surface of the gastric contents and forms a physical barrier to gastric reflux, and precedes stomach contents into the esophagus.

The gas-producing material is present in an amount so as to provide an adequate volume of gas to float the alginic acid gel formed when the magnesium alginate composition is contacted with the gastric contents, and most preferably in an amount equal to about one-eighth to about one-third the weight of magnesium alginate. It will be understood that the rigidity, strength and thickness of the foamy mass formed in contact with gastric acid will depend upon the ratio of bicarbonate to magnesium alginate, and upon the viscosity of the magnesium alginate.

A special embodiment of the present invention comprises a foamy mass forming composition including the gas producing material and a mixture of two or more viscosity grades of magnesium alginate. The use of two or more viscosity grades of the alginate provides for a stable, well-knitted raft. A preferred composition comprises three parts of a high viscosity magnesium alginate such as a viscosity of between about 900 and about 1400 cps (7.5 wt percent solution) and two parts of low viscosity magnesium alginate such as viscosity of between about 80 to about 150 cps (7.5 wt percent solution). The combination of the high and low viscosity grades results in a mixture of short and long alginate polymer chains and a viscosity as measured by a 5 wt percent solution of between about 100 to about 250 cps and preferably about 200 cps.

Another aspect of the present invention relates to the nature of the antacid material used in an aqueous suspension of the composition. By way of background, known floating antacid compositions include relatively small amounts of antacid material in amounts which can only neutralize a limited amount of acid and would not substantially change the gastric pH. Compositions of the present invention may include an amount of antacid material which can neutralize excess gastric acid present in the stomach. Suspensions of the type here involved should be stable for relatively long periods of time, such as one to two years, or at least be capable of being reconstituted by agitation subsequent to separation. In dilute suspensions, the coating-out of a "suspendant" is a minor problem but in more concentrated compositions it can be a major problem. Furthermore, under certain conditions, aqueous suspensions including two antacids such as magnesium carbonate and aluminum hydroxide tend to interact and selectively separate one suspendant, such as magnesium carbonate. The antacid material is preferably present in the composition in a form which minimizes the interaction.

Both of the foregoing problems can be inhibited or deterred according to the present invention by the use of a suspension stabilizer and the use of a combined form of magnesium carbonate and aluminum hydroxide. The suspension stabilizer is included in an amount which is effective to maintain the antacid material in suspension. The choice of stabilizer will depend on various factors, including the amount and viscosity grade of the magnesium alginate used in the composition and the amount, density and particle size of the antacid material. Preferably, the aqueous suspensions contain from 0.1 to 1.5% weight/volume of any pharmaceutically acceptable stabilizer which preferably does not contain sodium. Exemplary suspension stabilizers include tragacanth, guar gum, avicel, solka-floc, pectin, pregelatinized potato starch, calcium carbonate, calcium saccharin, citric acid, or hydroxypropylmethylcellulose.

It is preferred that the aqueous suspensions of the present invention have a long shelf life and not be subject to deterioration by microorganisms. Consequently the liquid compositions should contain a preservative. A combination of methyl and propyl p-hydroxybenzoates (methyl and propyl paraben) may be employed, for example, in an amount of 0.1% and 0.05% weight/volume, respectively. Antioxidants may also be included in the suspension to prevent discoloration over time.

The pharmaceutical compositions of the present invention may also include one or more of a coloring, sweetening or flavoring agent.

Tablet compositions according to the present invention may include binding agents and other ingredients known in the art to facilitate mixing, compressing, improved palatability and long term stability of the tablet.

A preferred composition according to the present invention comprises:

magnesium alginate comprising about 28 to about 35 wt % mannuronic acid and about 65 to about 72 wt % guluronic acid;

an efective acid-neutralizing amount of an antacid which comprises a first portion of magnesium carbonate, and a second portion of magnesium carbonate present in combined form with aluminum hydroxide in an amount, measured as MgO, of about 5 to about 20 wt %;

a gas-evolving material capable of producing a nontoxic gas when contacted with aqueous acid and in an amount such that the weight ratio of said magnesium alginate to said gas-evolving material is about 3:1 to about 8:1;

wherein the weight ratio of said magnesium alginate to said antacid is about one-half to about one.

A most preferred composition comprises said first portion of magnesium carbonate and said combined form of antacid material present in the composition in a ratio of about 1:1 to about 3:4.

A preferred aqueous suspension includes an effective amount of suspension stabilizer as described above and exhibits and acid-neutralizing capacity of about 1 to about 3 mEq/ml and a viscosity of about 100 to about 300 centipoise.

A particularly preferred suspension according to the present invention comprises about 30 to about 90 mg/ml of magnesium alginate, about 10 to about 50 mg/ml of magnesium carbonate, about 10 to about 50 mg/ml of a combined form of aluminum hydroxide and magnesium carbonate and about 2 to about 20 mg/ml of potassium bicarbonate.

The present invention is illustrated by the following examples.

EXAMPLE 1

The following suspension formulation is prepared using an amount of water such that each 5 ml dosage amount of suspension includes the indicated amounts of ingredients.

|  | mg/5 ml |
|---|---|
| Magnesium Alginate (200 cps/5% w/v solution) | 250 |
| Magnesium Carbonate USP | 160 |
| Aluminum Hydroxide-Magnesium Carbonate Gel (coprecipitated) | 180 |
| Potassium Bicarbonate USP | 50 |
| Methyl Paraben USP | 5 |
| Propyl Paraben USP | 2.5 |
| Sodium Saccharin NF | 1.4 |
| Sorbitol USP | 100 |
| Flavor | q.s. |

The resulting product has a smooth consistency, is pourable and is physically and chemically stable over a period of six months at ambient temperature. The suspension has an acid neutralizing capacity of about 8.2 mEq/5 ml (about 1.6 mEq/ml) and a sodium content of less than 4 mg per 5 ml.

Examples 2 through 7 describe other suspension formulations according to the present invention.

EXAMPLE 2

|  | mg/5 ml |
|---|---|
| Magnesium Alginate (200 cps/5% w/v solution) | 250 |
| Aluminum Hydroxide (wet gel) USP | 336 (dried basis) |
| Potassium Bicarbonate USP | 100 |
| Methyl Paraben USP | 5 |
| Propyl Paraben USP | 2.5 |
| Sodium Saccharin NF | 1.4 |
| Sorbitol USP | 100 |
| Flavor | q.s. |

EXAMPLE 3

|  | mg/5 ml |
|---|---|
| Magnesium Alginate (200 cps/5% w/v solution) | 250 |
| Magnesium Carbonate USP | 160 |
| Aluminum Hydroxide (dried gel) USP | 180 |
| Potassium Bicarbonate USP | 50 |
| Methyl Paraben USP | 5 |
| Propyl Paraben USP | 2.5 |
| Sodium Saccharin NF | 1.4 |
| Sorbitol USP | 100 |
| Flavor | q.s |

EXAMPLE 4

|  | mg/5 ml |
|---|---|
| Magnesium Alginate (200 cps/5% w/v solution) | 250 |
| Hydrotalcite | 350 |
| Potassium Bicarbonate USP | 50 |
| Methyl Paraben USP | 5 |
| Propyl Paraben USP | 2.5 |
| Sodium Saccharin NF | 1.4 |
| Sorbitol USP | 100 |
| Flavor | q.s. |

EXAMPLE 5

|  | mg/5 ml |
|---|---|
| Magnesium Alginate (200 cps/5% w/v solution) | 250 |
| Magnesium carbonate USP | 160 |
| Aluminum Hydroxide Magnesium Carbonate Gel (coprecipitated) | 180 |
| Potassium Bicarbonate USP | 50 |
| Hydroxypropylmethylcellulose USP | 25 |
| Methyl Paraben USP | 5 |
| Propyl Paraben USP | 2.5 |
| Sodium Saccharin NF | 1.4 |
| Sorbitol USP | 100 |
| Flavor | q.s. |

EXAMPLE 6

|  | mg/5 ml |
|---|---|
| Magnesium Alginate (200 cps/5% w/v solution) | 250 |
| Magnesium Carbonate NF | 160 |
| Aluminum Hydroxide-Magnesium Carbonate Gel (coprecipitated) | 180 |
| Potassium Bicarbonate USP | 50 |
| Tween 80 USP | 2.5 |
| Methyl Paraben USP | 5 |
| Propyl Paraben USP | 2.5 |
| Sodium Saccharin NF | 1.4 |
| Sorbitol USP | 100 |
| Flavor | q.s. |

EXAMPLE 7

| | mg/5 ml |
|---|---|
| Magnesium Alginate (200 cps/5% w/v solution) | 250 |
| Aluminum Hydroxide gel USP | 336 (dried basis) |
| Potassium Bicarbonate USP | 100 |
| Hydroxy Propyl Methylcellulose USP | 25 |
| Methyl Paraben USP | 5 |
| Propyl Paraben USP | 2.5 |
| Sodium Saccharin NF | 1.4 |
| Sorbitol USP | 100 |
| Flavor | q.s |

The following examples relate to tablet formulations.

EXAMPLE 8

Half strength tablet formulations are prepared from the following formulations.

| | mg/tablet |
|---|---|
| Magnesium Alginate (1000–1700 cps/7.5% w/v solution) | 250 |
| Magnesium Carbonate USP | 160 |
| Codried Aluminum Hydroxide - Magnesium Carbonate | 180 |
| Potassium Bicarbonate Powder USP | 50 |
| Compressible sugar NF | 750 |
| Pregelatinized starch USP | 55 |
| Magnesium Stearate NF | 14 |
| Flavor powder | q.s |

EXAMPLE 9

| | mg/tablet |
|---|---|
| Magnesium Alginate (1000–1700 cps/7.5% w/v solution) | 250 |
| Magnesium Carbonate USP | 160 |
| Aluminum Hydroxide - Magnesium Carbonate Gel (coprecipitated) | 180 |
| Compressible sugar NF | 750 |
| Potassium Bicarbonate Powder USP | 50 |
| Magnesium Stearate NF | 14 |
| Flavor powders | q.s. |

EXAMPLE 10

| | mg/tablet |
|---|---|
| Magnesium Alginate (1000–1700 cps/7.5% w/v solution) | 250 |
| Aluminum Hydroxide USP | 336 |
| Potassium Bicarbonate powder USP | 50 |
| Compressible sugar NF | 750 |
| Magnesium Stearate NF | 14 |
| Pregelatinized starch USP | 55 |
| Flavor powders | q.s. |

EXAMPLE 11

| | mg/tablet |
|---|---|
| Magnesium Alginate (1000–1700 cps/7.5% w/v solution) | 250 |
| Aluminum Hydroxide USP | 180 |
| Magnesium Hydroxide USP | 110 |
| Potassium Bicarbonate USP | 50 |
| Compressible sugar NF | 750 |
| Pregelatinized starch USP | 55 |
| Magnesium Stearate NF | 14 |
| Flavor powders | q.s. |

EXAMPLE 12

| | mg/tablet |
|---|---|
| Magnesium Alginate (1000–1700 cps/7.5% w/v solution) | 250 |
| Magnesium Carbonate USP | 160 |
| Aluminum Hydroxide USP | 180 |
| Compressible Sugar NF | 750 |
| Potassium Bicarbonate USP | 50 |
| Pregelatinized Starch USP | 55 |
| Magnesium Stearate NF | 14 |
| Flavor powders | q.s. |

EXAMPLE 13

| | mg/tablet |
|---|---|
| Magnesium Alginate (1000–1700 cps/7.5% w/v solution) | 250 |
| Hydrotalcite | 350 |
| Compressible sugar NF | 750 |
| Potassium Bicarbonate USP | 50 |
| Pregelatinized starch USP | 55 |
| Magnesium stearate NF | 14 |
| Flavor, powders | q.s. |

EXAMPLE 14

A full strength tablet is prepared by doubling the amounts of ingredients in the tablet examples above.

The tablet of Example 9 is prepared by mixing the ingredients together and compressing the mixture into tablet form.

The tablet of Examples 8 and 10 through 13 is prepared as follows:

All ingredients listed above except magnesium stearate are screened to eliminate unacceptably large particles. The screened ingredients are placed in a suitable mixer and blended. The resultant mixed granulate is wetted with less than about one ml of deionized water per full strength tablet and placed on trays in an oven to dry to an appropriate moisture level. The dried granulate is milled through an appropriate screen. Magnesium stearate is screened and blended with the dried granulate. The blended mix is compressed into tablets.

A further optional ingredient for incorporation into the tablet formulation comprises a mild carboxylic acid, such as alginic acid. The acid functions to provide a sensation of fizzing in the mouth while chewing the tablet. The amount of the acid is directly dependent on the desired intensity of the fizzing sensation and increases in accordance with the increased fizzing action. If the desired fizzing action is substantial, then the amount of carbonate-containing antacid material in the tablet is also increased so as to provide a sufficient source of carbon dioxide in the mouth as well as in the stomach. The additional carbonate-containing antacid material may comprise about an acid equivalent amount of material.

We claim:

1. A method for the treatment of reflux esophagitis in patients who restrict their dietary intake of sodium, comprising the administration thereto of an effective gastric reflux suppressive amount of a composition which is substantially sodium-free, and which is capable of forming a floating gelatinous mass when contacted with aqueous acid, said composition comprising magnesium alginate, an effective acid-neutralizing amount of an antacid, and an effective gas-volume-producing amount of non-toxic gas-producing material.

2. A method according to claim 1 wherein said gas-producing material is potassium bicarbonate.

3. A method according to claim 2 wherein said antacid comprises magnesium carbonate and aluminum hydroxide.

4. A method according to claim 3 wherein the amount of said magnesium alginate is about 8:1 to about 3:1 the weight of the amount of said potassium bicarbonate, and wherein the total amount of said magnesium carbonate and said aluminum hydroxide is about 2 to about 1 times the weight of said magnesium alginate.

5. A method according to claim 2 wherein said composition is an aqueous suspension having an acid-neutralizing capacity of about 1 to about 3 mEq/ml and a viscosity of about 100 to about 300 centipoise.

6. A method according to claim 5 wherein said suspension comprises:
about 30 to about 90 mg/ml of magnesiun alginate;
about 10 to about 50 mg/ml of magnesium carbonate;
about 10 to about 50 mg/ml of a combined form of aluminum hydroxide and magnesium carbonate; and
about 2 to about 20 mg/ml of potassium bicarbonate.

7. A method according to claim 6 wherein said combined form is prepared by drying an aqueous slurry of magnesium carbonate and aluminum hydroxide.

8. A method according to claim 7 wherein:
said aluminum hydroxide (as $Al_2O_3$) comprises about 25 to about 45 wt % of said combined form; and
said magnesium carbonate (as MgO) comprises about 5 to about 20 wt % of said combined form.

9. A method for the treatment of reflux esophagitis in patients restricting their dietary intake of sodium, comprising the administration thereto of an effective gastric reflux suppressive amount of a composition which is substantially sodium-free, and which is capble of forming a floating gelatinous mass when contacted with aqueous acid, said composition comprising
magnesium alginate comprising about 28 to about 35 wt % mannuronic acid and about 65 to about 72 wt % guluronic acid:
an effective acid-neutralizing amount of an antacid which comprises a first portion of magnesium carbonate, and a second portion of magnesium carbonate present in combined form with aluminum hydroxide in an amount, measured as MgO, of about 5 to about 20 wt %;
a gas-evolving material capable of producing a non-toxic gas when contacted with aqueous acid and in an amount such that the weight ratio of said magnesium alginate to said gas-evolving material is about three to about eight;
wherein the weight ratio of said magnesium alginate to said antacid is about one-half to about one.

10. A method according to claim 9 wherein the ratio of said first portion of magnesium carbonate to said combined form is about 1:1 to about 3:4.

11. A method according to claim 1 wherein the weight amount of said magnesium alginate is about three to about eight times the weight amount of said gas-producing material, and wherein the weight amount of said antacid material is about one to about two times the weight amount of said magnesium alginate.

12. A method according to claim 11 wherein said antacid material is selected from the group consisting of MgOH, $MgCO_3$, $Al(OH)_3$, Mg silicate, magaldrate and mixtures thereof.

13. A method for the treatment of reflux esophagitis in patients who restrict their dietary intake of sodium, comprising the administration thereto of an effective gastric reflux suppressive amount of a composition, which is substantially sodium-free and which is capable of forming a composition, comprising magnesium alginate, an antacid in an effective acid-neutralizing amount which is about one to two times the weight amount of said magnesium alginate, and a non-toxic gas-producing material in an effective gas-volume-producing amount which is about one-third to about one-eighth the weight amount of said magnesium alginate, and wherein said antacid material is selected from the group consisting of MgOH, $MgCO_3$, $Al(OH)_3$, Mg silicate, magaldrate and mixtures thereof.

* * * * *